United States Patent [19]

Stults et al.

[11] Patent Number: 5,675,039

[45] Date of Patent: Oct. 7, 1997

[54] BIS-M-BENZOTRIFLUORIDE COMPOUNDS

[76] Inventors: Jeffrey S. Stults, 1042 Baseline Rd.; Henry C. Lin, 1971 Ruth Rd.; Robert A. Buchanan, 2227 Center Ter. #1, all of Grand Island, N.Y. 14072

[21] Appl. No.: 554,222

[22] Filed: Apr. 15, 1996

Related U.S. Application Data

[60] Division of Ser. No. 594,479, Oct. 9, 1990, Pat. No. 5,498,691, which is a continuation-in-part of Ser. No. 394,990, Aug. 17, 1989, abandoned.

[51] Int. Cl.$^6$ .................... C07C 225/22; C07C 317/36
[52] U.S. Cl. .................... 564/328; 564/430; 568/30; 568/36; 568/44; 568/306; 568/585
[58] Field of Search .................... 564/430, 328

[56] References Cited

U.S. PATENT DOCUMENTS

| | | | |
|---|---|---|---|
| 4,996,278 | 2/1991 | Lee | 528/26 |
| 5,061,781 | 10/1991 | Leone-Bay et al. | 528/179 |
| 5,484,879 | 1/1996 | Buchanan et al. | 528/353 |

*Primary Examiner*—Richard L. Raymond
*Attorney, Agent, or Firm*—Richard D. Fuerle; Arthur S. Cookfair

[57] ABSTRACT

Disclosed are bis-meta-benzotrifluoride compounds having the general formula

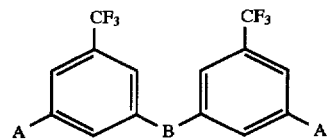

where each A is independently selected from the group consisting of $NO_2$, $NH_2$, and $NH_3^+Z^-$, $Z^-$ is an anion and B is selected from the group consisting of O, CO, S, SO, and $SO_2$. The diamine compounds are useful as monomers in making polyimides, polyamide-imides, and polyamides.

11 Claims, No Drawings

BIS-M-BENZOTRIFLUORIDE COMPOUNDS

This application is a division of application Ser. No. 07/594,479, filed Oct. 9, 1990, now U.S. Pat. No. 5,498,691, which is a continuation-in-part of application Ser. No. 07/394,990, filed Aug. 17, 1989, now abandoned.

BACKGROUND OF THE INVENTION

This invention relates to novel bis-m-benzotrifluoride compounds. In particular, it relates to bis-m-benzotrifluoride diamines, precursors for making the diamines, and to polymers made from the diamines.

Polyimides are condensation polymers usually made by reacting a primary diamine with a dianhydride or tetracarboxylic acid. Aromatic polyimides, where both the diamine monomer and the dianhydride or tetracarboxylic acid monomer are aromatic, exhibit outstanding mechanical properties and excellent thermal and oxidative stability. They are widely used in place of metals and glass in high performance applications throughout the electrical, electronic, automotive, aerospace, and packaging industries.

The properties of a particular polyimide depend, of course, on the particular diamines and dianhydrides or tetracarboxylic acids used in making it. Properties that are very useful in the electronics industry include a high solubility of the polyimide in organic solvents and a low dielectric constant. If the polyimide is to be used as a film, it is desirable that it be colorless and transparent so that the underlying substrate is visible and undistorted.

SUMMARY OF THE INVENTION

We have discovered and made a new class of diamines, and precursors for making those diamines, which are very useful as monomers in making polyimides. The diamines of this invention contain two benzotrifluoride groups which give the resulting polyimides excellent electronic properties, particularly a high solubility in organic solvents and a low dielectric constant. Unlike other benzotrifluoride diamines known in the art, the benzotrifluoride diamines of this invention are meta-benzotrifluoride diamines which means that the substituents on the benzene ring are in the 1,3,5 positions. Because the substituents are meta, the resulting polyimides are much more stable than similar, but non-meta, benzotrifluoride diamines.

DESCRIPTION OF THE INVENTION

The novel meta-benzotrifluoride compounds of this invention have the general formula

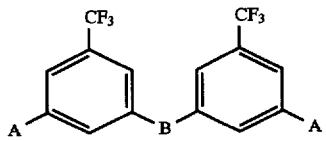

where A is $NO_2$, $NH_2$, or $NH_3^+Z^-$, and B is O, CO, S, SO, or $SO_2$. The nitro compounds (where A is $NO_2$) are intermediate compounds used to make the diamine. When A is $NH_3^+Z^-$, an amine salt is formed where Z is an anion. Examples of suitable anions include chloride, bromide, sulfate, and bisulfate. The chloride anion is preferred as compounds necessary to make the chloride salt are inexpensive and readily available. In the above formula, B is preferably O, CO, or $SO_2$ as those compounds are the most useful in making polyimides.

The diamines of this invention can be prepared by a variety of methods, the appropriateness of a method depending upon the particular diamine that is being prepared. The ether (where B is O) can be prepared by heating 3,5-dinitrobenzotrifluoride in an organic solvent in the presence of water and about two equivalents (based on the product weight) of potassium or cesium fluoride which results in the dinitrodibenzotrifluoride ether:

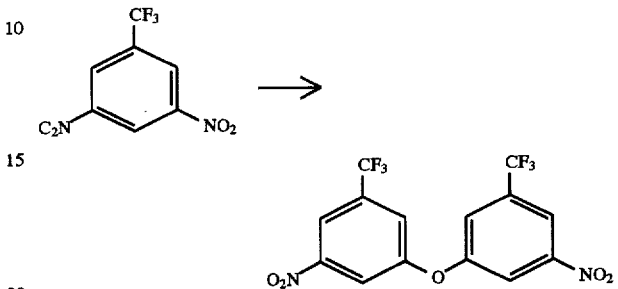

1,1'-oxybis(3-nitro-5-trifluoromethyl) benzene In this reaction, it is preferable to use potassium fluoride as a catalyst and N,N-dimethylformamide (DMF) as a solvent and to heat at a temperature between about 120° and 160° C. The reaction also produces small amounts of higher ethers.

The ether can also be prepared by heating a nitro benzotrifluoride compound having the formula

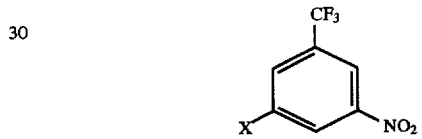

where x is $NO_2$, Cl, F, or a mixture thereof, with potassium fluoride, cesium flouride, or a mixture thereof, as described in copending application Ser. No. 394,986, filed Aug. 17, 1989, now U.S. Pat. No. 4,990,670, by the same inventors, herein incorporated by reference.

The diamine can be prepared from the corresponding dinitro compound by heating in a reducing agent, such as about 10 to about 50% iron and about 1 to about 20% hydrochloric acid:

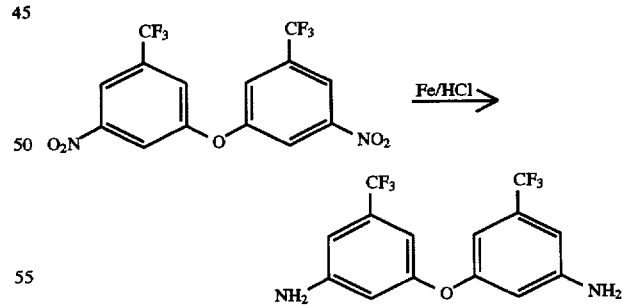

4,4'-oxybis(3-trifluoromethyl)-benzamine

That reaction can be performed at a temperature of about 0 to about room temperature; ammonium sulfide can also be used as a reducing agent. The presence of an acid in the reduction reaction results in the formation of an amide salt (i.e., A is $NHNH_3^+Z^-$). The amine salt can be easily converted to the amine by the addition of any base such as sodium hydroxide, triethyl amine, or pyrridine.

The ketone diamine (where B is CO) can be prepared by reacting dibenzotrifluoride ketone with fuming nitric acid in the presence of fuming sulfuric acid to first produce the dinitro ketone:

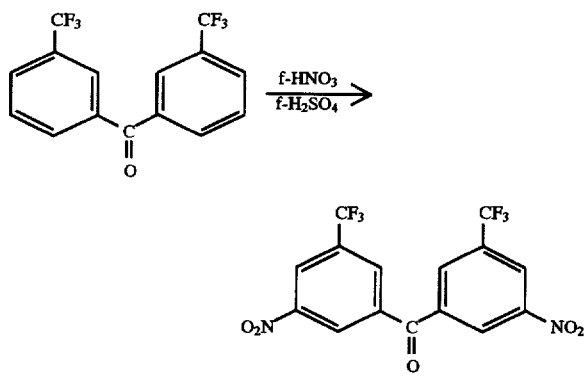

The reaction should be conducted at a temperature of less than 60° C. to prevent the formation of undesirable products.

The dinitro ketone can be reduced by the same reduction reaction described hereinabove to produce the diamino ketone, 3,3'-ketobis (5-trifluoromethyl)-benzamine (KBABTF).

The sulfide compound (where B is S) can be prepared by reacting dinitrobenzotrifluoride with sodium sulfide or potassium sulfide to first produce the dinitro sulfide:

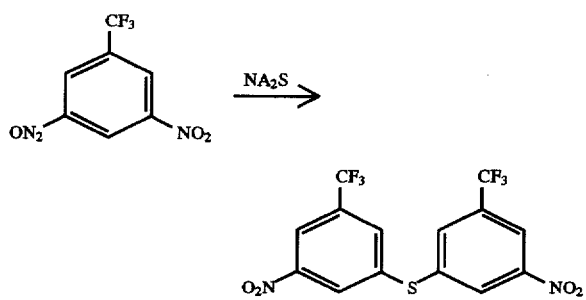

1,1'-thiobis(3-nitro-5-trifluoromethyl)-benzene

That reaction can be conducted at about 150° C. for about four hours and can be followed by gas chromatograph (GC). The yield from that reaction is about 10%. The dinitro sulfide can be reduced to the diamino sulfide by the reduction reaction hereinbefore described.

The sulfoxide (where B is SO) can be made by oxidizing the diamino sulfide compound. This can be accomplished with an oxidizing agent such as hydrogen peroxide or, more preferably, metachloroperbenzoic acid, at a temperature of less than 0° C.

The sulfone compound (where B is SO₂) can be prepared by reacting benzotrifluoride, meta-chloride with sodium sulfide to prepare dibenzotrifluoride sulfide:

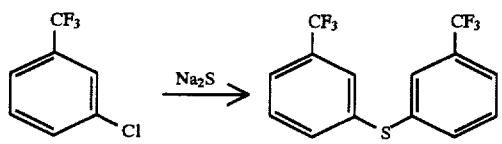

This reaction is performed in an organic solvent such as NMP at a temperature of about 170° C. In the next step, the sulfide is oxidized to the sulfone using an oxidizing agent such as 30% hydrogen peroxide in acetic acid in a concentration of 30%:

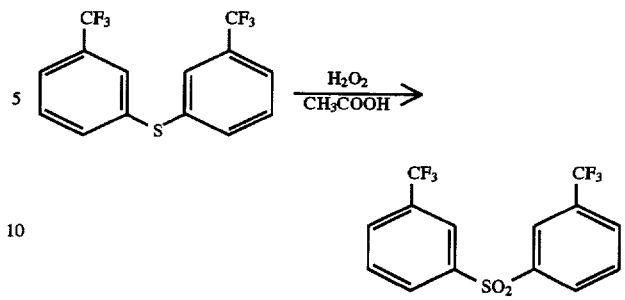

These first two steps are reactions known in the art, see Example 17 of U.S. Pat. No. 3,538,166 and an article by J. R. Campbell and R. E. Hatton in *J. Org. Chem.* 26, p. 2480 (1961).

In the next step, the sulfone is nitrated using a mixture of at least two equivalents nitric acid (density—1.5 g/cc or greater) and at least two equivalents sulfuric acid containing up to 65% SO₃ at a temperature of less than 80° C.:

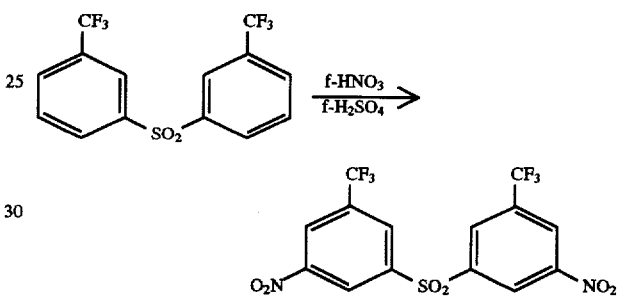

1,1'-sulfonyl bis(3-nitro-5-trifluoromethyl) benzene

Finally, the dinitro compound is reduced to the amine compound by the hereinabove-described reduction reaction.

A second way of making the sulfone is described in copending patent application Ser. No. 394,988, filed Aug. 17, 1989, now U.S. Pat. No. 5,304,687, by Jeffrey S. Stults, titled "Method of Making Dinitro and Diamino Meta-Bisbenzotrifluoride Compounds," herein incorporated by reference. Briefly, dibenzotrifluoride sulfide is reacted with fuming nitric acid in the presence of fuming sulfuric acid at a temperature of about 0° to about 75° C.:

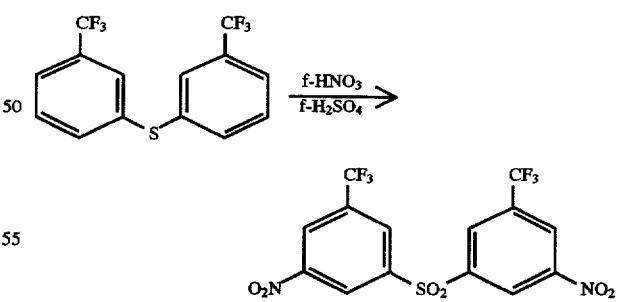

The diamines of this invention are useful in making polyimides, polyamide-imides, and polyamides. The polyimides can be prepared by well-known reactions of diamines with dianhydrides or tetracarboxylic acids, substituting the diamines of this invention for the diamines that would otherwise be used. While non-aromatic dianhydrides can be used, aromatic dianhydrides are preferred because the polyimides have better thermal properties. Examples of suitable dianhydrides include oxydiphthalic anhydride (ODPA), biphenyl dianhydride (BPDA), benzophenone tetracarboxylic dianhydride (BTDA), pyromellitic dianhydride (PMDA), and "6-F" dianhydride 5,5'-[2,2,2-trifluoro-1-(trifluoromethyl)ethylidene] bis-1,3-isobenzofurandione). Generally, the reaction of the diamine and the dianhydride or tetracarboxylic acid will proceed at room temperatures or under mild heat. Dianhydrides are preferred to tetracarboxylic acids as the reaction proceeds more easily. Polyimides can also be prepared from half esters of tetracarboxylic acids and from hydrolyzed nitriles, but the reactions are more difficult. Polyamideimides can be prepared by reacting the diamines with a trifunctional anhydride or carboxylic acid such as trimellitic anhydride or trimellitic acid. Polyamides can be prepared by reacting the diamine with a dicarboxylic acid or an acid halide, and polyurethanes can be prepared by reacting the diamines with diisocyanate.

The following examples further illustrate this invention.

EXAMPLE 1

Preparation of 1,1'-sulfonyl-bis(3-nitro-5-trifluoromethyl)benzene

To a one liter flask was charged nitric acid (fuming, 50 ml.) and sulfuric acid (20% oleum, 130 ml.) and the flask was cooled to 0°–5° C. with an ice bath. 1,1'-Sulfonyl-bis (3-trifluoromethyl)benzene (23.5 g.) was added. The reaction mixture was heated to 65° C. and after 3 hours GC analysis indicated complete consumption of the sulfone and appearance of 1-(3-nitro-5-trifluoromethylphenylsulfonyl)-3-trifluoromethylbenzene. Nitric acid (fuming, 75 ml.) and sulfuric acid (20% oleum, 195 ml.) were added and the reaction was heated for an additional 5 hours. The reaction mixture was purged with nitrogen until evolution of nitrogen oxides ceased. The reaction mixture was poured into 400 g. ice and the resulting solid collected. The solid was washed with cold water to give 26.8 g (91% yield) of the desired 1,1-sulfonyl-bis(3-nitro-5-trifluoromethyl)benzene.

EXAMPLE 2

Preparation of 1,1'-oxybis(3-nitro-5-trifluoromethyl) benzene

To a 500 ml round bottom flask was charged 3,5-dinitrobenzotrifluoride (25.1 g.), potassium fluoride (21.2 g), water (2.4 ml.), and dimethylformamide (DMF, 125 ml.). The reaction was heated to 160° C. for 24 hours. The reaction mixture was diluted with water (400 ml.) and extracted with ether (3×150 ml.). The ether was dried with magnesium sulfate and cooled to 5° C. and the resulting solid collected to give a total of 11.3 g (53.8% yield) of the desired 1,1-oxy-bis(3-nitro-5-trifluoromethyl)benzene.

EXAMPLE 3

Preparation of 4,4'-oxybis(3-trifluoromethyl)-benzamine hydrochloride

To a flask containing about 0.88 g of the product of Example 2 was added 1.8 g iron powder and 10 ml of 50% ethanol. The mixture was heated to reflux and 1.5 ml of 50% ethanol and 0.1 ml concentrated HCl was added. The mixture was refluxed for 2 hours. The iron powder was filtered and washed with 95% ethanol. The ethanol was evaporated, water was added, and the product was extracted with ether. Hydrogen chloride was bubbled through the ether solution of the product and 0.38 g of 4,4'-oxybis(3-trifluoromethyl)-benzamine hydrochloride (43% yield) were collected.

EXAMPLE 4

Preparation of 1,1'-sulfonyl-bis (3-nitro-5-trifluoromethyl)benzene

To a cooled (10° C.) 250 ml. round bottom flask containing nitric acid (fuming, 50 ml.) and sulfuric acid (20% oleum, 90 ml.) was added 1,1'-thio-bis(3-trifluoromethyl) benzene (10 g). The reaction mixture was held at low temperature until sulfoxide formation was complete (circa 1.5 hrs) and then heated to 35° C. The reaction mixture was then heated slowly to 65° C. Analysis of the reaction mixture indicated a mixture of nitrated compounds had formed. The oxidation and nitration reactions were carried to completion by heating the reaction mixture to 85° C. The reaction mixture was then poured onto ice and the solid collected and washed with cold water to give 1,1'-sulfonyl-bis)3-nitro-5-trifluoromethyl)benzene as a white solid (7.16 g, 52% yield).

EXAMPLE 5

Preparation of 1,1'-sulfonyl-bis (3-nitro-5-trifluoromethy)benzene

To a cooled (10° C.) 250 ml. round bottom flask containing nitric acid (fuming, 50 ml.) and sulfuric acid (20% oleum, 90 ml.) was added 1,1'-sulfonyl-bis(3-trifluoromethyl)benzene (27.3 g). The reaction mixture was heated to 75° C. and additional nitric acid (52 ml.) and sulfuric acid (130 ml.) were added. The reaction was heated for 7 hours at 75° C. and additional nitric acid (3 ml.) and sulfuric acid (3 ml.) was then added. The reaction mixture was heated for an additional 2 hours. The reaction mixture was poured onto 600 g. ice and the collected solid was washed with cold water to give 1,1'-sulfonyl-bis(3-nitro-5-trifluoromethyl)benzene as a white solid (27.2 g, 79% yield). Additional 1,1'-sulfonyl-bis(3-nitro-5-trifluoromethyl) benzene could be obtained from an ether extraction of the filtrate (4.4 g, 92% total yield).

EXAMPLE 6

Preparation of 5,5'-bistrifluoromethy-3,3'-dinitro-benzophenone

To a 250 ml. flask containing nitric acid (fuming 33.8 g.) and sulfuric acid (20% oleum, 83 ml.) was added first 3,3'-bistrifluoromethyl benzophenone (40.6 g.) followed by additional sulfuric acid (50 ml.). The temperature was maintained at less than 40° C. by cooling with an ice water bath. The reaction mixture was heated at 40° C. for approximately 3 hours. The reaction mixture was poured onto 300 g. ice and the precipitate was collected, washed with cold water, and dried to give 5,5'-bistrifluoromethyl-3,3'-dinitro benzophenone (51.4 g., 82% yield).

EXAMPLE 7

Preparation of 3,3'-thiobis(3-nitro-5-trifluoromethyl) benzene

A 25 ml 2-necked flask was charged with 0.44 g $Na_2S$ nonahydrate, and 2 ml NMP. The mixture was heated to 210° C. to remove water and 0.99 g of meta-dinitrobenzotrifluoride was added. The yield of 3,3'-thiobis (3-nitro-5-trifluoromethyl)benzene was about 10%.

EXAMPLE 8

Preparation of 5,5'-bistrifluoromethyl-3,3'-diaminobenzophenone, hydrochloride salt To a round bottom flask containing ethanol (80 ml.) and 5,5'-bistrifluoromethyl-3,3'-dinitro benzophenone (4.9 g.) at 50° C. was added 10% palladium on carbon (0.05 g.) followed by hydrazine (3.0 ml.). The reaction temperature was raised to 70° C. and the reaction stirred for 2 hours. The reaction mixture was filtered through filter aid, the ethanol removed under reduced pressure, and replaced with ethyl acetate (90 ml.). The ethyl acetate was washed with a saturated sodium chloride solution (10 ml.), followed by water (10 ml.) and saturated sodium chloride solution. The ethyl acetate was dried (sodium sulfate) and evaporated to give a residue (3.62 g.). The residue was dissolved in ether and the ether was washed with 10% aqueous HCl followed by a 5% aqueous bicarbonate solution. Hydrogen chloride gas was then bubbled through the ether solution to give 5,5'-bistrifluoromethyl-3,3'-diamino benzophenone, hydrochloride salt as a precipitate (2.1 g, 50% yield).

EXAMPLE 9

Preparation of 1,1'-oxybis(3-nitro-5-trifluoromethyl) benzene

The following experiment was conducted to determine if the other leaving groups could be used in place of nitro for the preparation of 1,1-oxybis(3-nitro-5-trifluoromethyl) benzene. To a solution of 3-fluoro-5-nitrobenzotrifluoride, isolated by distillation from the mother liquor of Example 2, in DMF (5 ml.) was added potassium fluoride (0.7 g.). The suspension was heated to 150° C. and 2 drops of water were added. The reaction progress was monitored by gas chromatography (GC). After 7 hours, GC analysis indicated a 0.17:1 mixture of 1,1-oxybis(3-nitro-5-trifluoromethyl) benzene to the starting fluoride had been obtained. This ratio increased to 2.1:1 after heating for 17.5 hours.

EXAMPLE 10

Preparation of Polyimide From 5,5'-oxybis (3-trifluoromethyl) benzamine(135-OBABTF) and ODPA ODPA (11.69 g) was added to a stirred solution of dry dimethylacetamide (76.1 g) containing 12.68 g of the diamine 135-OBABTF. The solution was stirred at room temperature under a nitrogen atmosphere for 16 to 24 hours. After filtration, a portion of the resulting poly(amic acid) solution was spread on a glass plate with a doctor blade to a 0.9 to 1.1 mil thick polyimide film after curing. The plate was placed in a dust-free chamber and warm nitrogen was passed over the plates until the film was no longer tacky. The plates were heated at a rate of 2° C. per minute and held at 100° C., 200° C., and 300° C. for 0.5 to 1 hour each to effect imidization. After cooling, the films were removed by soaking in warm to hot water. The cured film was transparent, creasible, and tough. $T_g$=210° C., dielectric constant=3.10 (1 MHz at 50% relative humidity), oxygen index=45.3%, 84% transmittance at 500 nm, and tensile modulus 480,000 psi.

EXAMPLE 11

Preparation of Polyimide From 135-OBABTF AND BTDA 9.20 g 135-OBABTF, 8.77 g BTDA, and 84.3 g DMAc were used as described above to give a tough, transparent polyimide with $T_g$=225° C., dielectric constant=2.99 (1 MHz, 50% relative humidity), moisture regain=0.46% (50% relative humidity), dissipation factor=0.0052 (1 MHz at 50% relative humidity), oxygen index=47.3%, and transmittance at 500 nm.

EXAMPLE 12

Preparation of Polyimide From 135-OBABTF AND BPDA 15.39 g 135-OBABTF, 13.40 g BPDA, and 90.0 g DMAc were used as described above to give a tough, transparent polyimide with $T_g$=240° C., dielectric constant=3.13 (1 MHz, 50% relative humidity), moisture regain=0.44% (50% relative humidity), dissipation factor=0.0045 (1 MHz at 50% relative humidity), oxygen index=49.5%, and 86% transmittance at 500 nm.

EXAMPLE 13

Preparation of Polyimide From 135-OBABTF AND 6FDA 9.93 g 135-OBABTF, 13.11 g 6FDA, and 86.2 g DMAc were used as described above to give a tough, transparent polyimide with $T_g$=230° C., dielectric constant=2.62 (1 MHz, 50% relative humidity), moisture regain=0.33% (50% relative humidity), dissipation factor=0.0065 (1 MHz at 50% relative humidity), and 88% transmittance at 500 nm.

EXAMPLE 14

Preparation of Polyimide From 135-SBABTF AND BTDA 1.4832 g 135-SBABTF, 1.4152 g BTDA, and 14.5 ml DMAc were used as described in Example 13 to give a poly(amic acid) with an inherent viscosity of 0.40. Upon curing as described above, a clear polyimide film was formed.

EXAMPLE 15

Preparation of Polyimide From 135-KBABTF AND ODPA 0.4769 g 135-KBABTF, 0.5151 g ODPA, and 5.0 ml DMAc were used as described above to give a poly(amic acid) with an inherent viscosity of 0.23. Upon curing as described above, a polyimide film was formed which was soluble in chloroform.

EXAMPLE 16

Preparation of Polyimide From 135-OBABTF AND ODPA 12.68 g 135-OBABTF, 11.69 g ODPA, and 76.1 g DMAc were used as described above to give a tough, transparent polyimide with a $T_g$=210° C., dielectric constant=3.10 (1 MHz, 50% relative humidity), moisture regain=0.33% (50% relative humidity), oxygen index=45.3%, thermal decomposition temperature of 548° C., and 78% transmittance at 500 nm.

EXAMPLE 17

Preparation of polyimides from 135-OBABTF AND BTDA 9.20 g 135-OBABTF, 8.77 g BTDA, and 84.3 g DMAc were used as described above to give a tough, transparent, polyimide with a $T_g$=225° C., dielectric constant=2.99 (12 MHz, 50% relative humidity), moisture regain=0.46% (50% relative humidity), oxygen index=47.3%, thermal decomposition temperature at 536° C., and 78% transmittance at 500 nm.

EXAMPLE 18

Preparation of Polyimide From 135-OBABTF AND BTDA 15.39 g 135-OBABTF, 13.40 g BTDA, and 90.0 DMAc were used as described above to give a tough transparent polyimide with at $T_g=240°$ C., dielectric constant=3.13 (1 MHz, 50% relative humidity), moisture regain=0.44% (50% relative humidity), oxygen index=49.5%, thermal decomposition temperature of 545° C., and 86% transmittance at 500 nm.

EXAMPLE 19

Preparation of Polyimide From 135-OBABTF AND BTDA 9.93 g 135-OBABTF, 13.11 g BTDA, and 86.2 g DMAc were used as described above to give a tough, transparent polyimide with a $T_g=230°$ C., dielectric constant=2.62 (1 MHz, 50% relative humidity), moisture regain=0.33% (50% relative humidity), thermal decomposition temperature of 528° C., and 88% transmittance at 500 nm.

COMPARATIVE EXAMPLES

EXAMPLE 20

Preparation of Polyimide From 124-OBABTF AND ODPA 12.43 g ODPA was added to a stirred solution of dry dimethylacetamide (121.8 g) containing 13.48 g of the diamine 124-OBABTF. The solution was stirred at room temperature under a nitrogen atmosphere for 12 to 20 hours. After filtration, a portion of the resulting poly(amic acid) solution was spread on glass plates with a doctor blade to give a 0.9 to 1.1 mil thick polyimide film after curing. The plates were placed in dust-free chamber and warm nitrogen was passed over the plates until the films were no longer tacky. The plates were heated at the rate of 2° C. per minute and held at 100° C., 200° C. and 300° C. for 0.5 to 1 hour each. After cooling, the films were removed by soaking in warm to hot water. The cured film was transparent, tough, and light yellow in color. The $T_g=255°$ C., dielectric constant=3.14 (1 MHz, 50% relative humidity), moisture regain=0.54% (50% relative humidity), and tensile modulus 457,000 psi.

EXAMPLE 21

Preparation of Polyimide From 124-OBABTF AND BTDA 10.08 g 124-OBABTF, 9.66 g BTDA, and 123.3 g DMAc were used as described above to give a tough, transparent polyimide with a $T_g=265°$ C., dielectric constant=3.22 (1 MHz, 50% relative humidity), moisture regain=0.70% (50% relative humidity), and 70% transmittance at 500 nm.

EXAMPLE 22

Preparation of Polyimide From 124-OBABTF AND BPDA 10.01 g 124-OBABTF, 8.76 g BPDA, and 117.1 DMAc were used as described above to give a tough, transparent polyimide with a $T_g=290°$ C., dielectric constant=3.20 (1 MHz, 50% relative humidity), moisture regain=0.67% (50% relative humidity), and 78% transmittance at 500nm.

EXAMPLE 23

Preparation of Polyimide From 124-OBABTF AND 6FDA 6.86 g 124-OBABTF, 9.06 g 6FDA, and 99.3 DMAc were used as described above to give a tough, transparent polyimide with at $T_g=295°$ C., dielectric constant=0.53% (1 MHz, 50% relative humidity), and 88% transmittance at 500 nm.

EXAMPLE 24

Preparation of Polyimide From 124-OBABTF AND 6FDA 14.50 g 124-OBABTF, 9.41 g 6FDA, and 112.0 g DMAc were used as described above to give a tough, transparent polyimide with a $T_g=315°$ C., dielectric constant=3.16 (1 MHz, 50% relative humidity), moisture regain=1.12% (50% relative humidity), thermal decomposition temperature of 548° C., and 80% transmittance at 500 nm.

The following table summarizes the results of Examples 10 to 24 and compares properties of polyimides prepared from 135 OBABTF with the properties of polyimides prepared from 24 OBABTF

|  | ODPA | | BTDA | | BPDA | | 6-FDA | |
|---|---|---|---|---|---|---|---|---|
|  | 135 OBABTF | 124 OBABTF | 135 OBABTF | 124 OBABTF | 135 OBABTF | 124 OBABTF | 135 OBABTF | 124 OBABTF |
| Glass transition temperature (°C.) | 210 | 255 | 225 | 256 | 240 | 290 | 230 | 295 |
| Dielectric constant (ASTM D150-87) | 3.1 | 3.14 | 2.99 | 3.22 | 3.13 | 3.2 | 2.62 | 2.76 |
| Moisture Regain (50% RH) | 0.0033 | 0.0054 | 0.0046 | 0.007 | 0.0067 | 0.0067 | 0.0033 | 0.0053 |
| Transmission (500 nm) | 84% | 85% | 78% | 70% | 86% | 78% | 88% | 88% |
| Tensile modulus (psi) | 480000 | 457000 | | | | | | |
| 10% weight loss (3°/min, air) | | | | | | | 528° C. | 524° C. |

In the above table, a low glass transition temperature, $T_g$, is desirable because polyimides having a low $T_g$ are more easily processed. The dielectric constant and the moisture regain should also be low for better electrical insulating properties. High light transmission is desirable for optical applications and for aesthetic reasons. A high tensile modulus provides strength and a high weight loss indicates thermal stability. the above table shows that the polyimides made from 135 OBABTF (i.e., the polyimides of this invention) have superior properties to polyimides made from 124 OBABTF.

We claim:

1. A meta-benzotrifluoride compound having the general formula

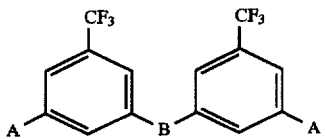

where each A is independently selected from the group consisting of $NH_2$ and $NH_3^+Z^-$, $Z^-$ is an anion, and B is selected from the group consisting of O, CO, S, SO, and $SO_2$.

2. A compound according to claim 1 wherein A is $NH_2$ and B is S.

3. A compound according to claim 1 wherein A is $NH_2$ and B is SO.

4. A compound according to claim 1 wherein A is $NH_2$ and B is $SO_2$.

5. A compound according to claim 1 wherein A is $NH_3^+Z^-$ and B is O.

6. A compound according to claim 1 wherein A is $NH_3^+Z^-$ and B is CO.

7. A compound according to claim 1 wherein A is $NH_3^+Z^-$ and B is S.

8. A compound according to claim 1 wherein A is $NH_3^+Z^-$ and B is SO.

9. A compound according to claim 1 wherein A is s $NH_3^+Z^-$ and B is $SO_2$.

10. A meta-benzotrifluoride diamine having the general formula

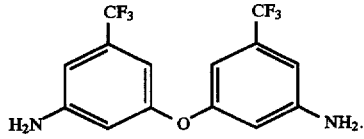

11. A meta-benzotrifluoride diamine having the general formula

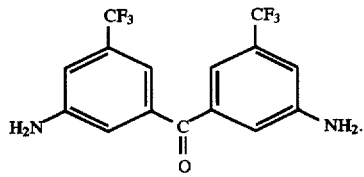

* * * * *